United States Patent
Sim et al.

(10) Patent No.: US 10,172,769 B2
(45) Date of Patent: Jan. 8, 2019

(54) METHOD FOR WHITENING TEETH

(71) Applicant: DENT-WHITE CO., LTD., Paju-si (KR)

(72) Inventors: Jae Hyun Sim, Paju-si (KR); Bong Kyu Choi, Seoul (KR); Yu Jung Choi, Chungju-si (KR); Hyung Kil Choi, Suwon-si (KR)

(73) Assignee: Quorum Bio Co., Ltd., Seoul (KR)

( * ) Notice: Subject to any disclaimer, the term of this patent is extended or adjusted under 35 U.S.C. 154(b) by 0 days.

(21) Appl. No.: 15/538,250

(22) PCT Filed: Jan. 6, 2016

(86) PCT No.: PCT/KR2016/000098
§ 371 (c)(1),
(2) Date: Jun. 21, 2017

(87) PCT Pub. No.: WO2016/111544
PCT Pub. Date: Jul. 14, 2016

(65) Prior Publication Data
US 2017/0367942 A1    Dec. 28, 2017

(30) Foreign Application Priority Data
Jan. 9, 2015   (KR) .................. 10-2015-0003496

(51) Int. Cl.
| | |
|---|---|
| *A61C 1/08* | (2006.01) |
| *A61K 8/02* | (2006.01) |
| *A61K 8/19* | (2006.01) |
| *A61K 8/20* | (2006.01) |
| *A61K 8/22* | (2006.01) |
| *A61K 8/23* | (2006.01) |
| *A61K 8/24* | (2006.01) |
| *A61N 1/04* | (2006.01) |
| *A61C 19/06* | (2006.01) |
| *A61Q 11/00* | (2006.01) |

(52) U.S. Cl.
CPC ............... *A61K 8/22* (2013.01); *A61C 1/08* (2013.01); *A61C 19/06* (2013.01); *A61K 8/0204* (2013.01); *A61K 8/19* (2013.01); *A61K 8/20* (2013.01); *A61K 8/23* (2013.01); *A61K 8/24* (2013.01); *A61N 1/04* (2013.01); *A61Q 11/00* (2013.01); *A61K 2800/434* (2013.01); *A61K 2800/81* (2013.01); *A61K 2800/83* (2013.01)

(58) Field of Classification Search
CPC ............... A61K 8/22; A61K 8/19; A61K 6/00
USPC ......................................... 433/215
See application file for complete search history.

(56) References Cited

U.S. PATENT DOCUMENTS

| | | | | |
|---|---|---|---|---|
| 5,785,527 A | * | 7/1998 | Jensen ................ | A61C 19/066 424/53 |
| 9,320,580 B2 | * | 4/2016 | Montgomery ....... | A61C 19/066 |
| 2005/0064370 A1 | * | 3/2005 | Duret .................. | A61C 19/066 433/215 |
| 2008/0003540 A1 | | 1/2008 | Khawaled et al. | |
| 2008/0044363 A1 | | 2/2008 | Montgomery | |
| 2008/0075676 A1 | | 3/2008 | MacDonald et al. | |
| 2013/0137063 A1 | | 5/2013 | Edwards | |
| 2013/0288203 A1 | | 10/2013 | Montogmery | |

FOREIGN PATENT DOCUMENTS

| | | |
|---|---|---|
| EP | 1295625 | 3/2003 |
| EP | 1542763 | 6/2005 |
| JP | 2009-102308 | 5/2009 |
| JP | 2010-062159 | 3/2010 |
| KR | 10-2005-0062557 | 6/2005 |
| KR | 10-0657127 | 12/2006 |
| KR | 10-2014-0054623 | 5/2014 |
| KR | 10-1536272 | 7/2015 |

OTHER PUBLICATIONS

KIPO, Search Report, Application No. of PCT/KR2016/000098, dated May 30, 2016.
EPO, The Extended European Search Report of EP 16735165.9 dated Dec. 12, 2017.

* cited by examiner

*Primary Examiner* — Walter E Webb
(74) *Attorney, Agent, or Firm* — Lex IP Meister, PLLC

(57) ABSTRACT

The present invention relates to a method for whitening teeth. The method for whitening teeth according to the present invention can promote the whitening activity of a tooth whitening agent and increase the degree of permeation of the whitening agent into the teeth, thereby obtaining an excellent whitening effect. Therefore, an excellent whitening effect can be obtained despite the use of low-concentration peroxide, compared with the use of high-concentration peroxide.

6 Claims, 2 Drawing Sheets

METHOD FOR WHITENING TEETH

BACKGROUND OF THE INVENTION

(a) Field of the Invention

The present invention relates to a method for whitening teeth. More specifically, the present invention relates to a method for whitening teeth capable of increasing both the degree of permeation of a whitening agent into the teeth and the whitening activity thereof, thereby obtaining an excellent whitening effect.

(b) Description of the Related Art

Since white teeth accounts for a large proportion of the appearance, there is a growing interest in tooth whitening worldwide.

Checking the causes of coloring of the tooth which is known up to now, they can be divided into an endogenous tooth discoloration caused by nerve damage inside the teeth, aging or excessive uptake of antibiotics such as tetracycline and the like, and extraneous tooth discoloration caused by food debris deposited on the tooth surface, or cigarette tar, coffee, tea and the like.

As the tooth whitening performed for improving the tooth discoloration, there are a method of home bleaching, which is a self-whitening method performed by oneself, and a method of office bleaching performed by an expert. As compared to the home bleaching, tooth whitening agents used for the office bleaching may contain a relatively high concentration of hydrogen peroxide, and an activation system such as heat and light is used for promoting tooth whitening effects. Since the system using heat has a risk of damaging the nerves of the teeth, in recent years, the system which uses light for promoting the tooth whitening effect is more preferred.

Basically, tooth whitening agents use hydrogen peroxide to decompose pigments deposited on the teeth, thereby whitening the teeth. As a higher concentration of hydrogen peroxide is used, a greater whitening effect is observed. That is, as the concentration of hydrogen peroxide increases, the degree of permeation into the teeth increases due to the difference in the concentration, and as the concentration increases, the amount of hydrogen peroxide that causes reaction increases, thereby increasing the decomposition performance of pigment, that is, the tooth whitening effect.

However, since hydrogen peroxide damages human skin and mucous membrane when its concentration is high, the concentration is strictly limited. For example, in Korea, in the case of home teeth whitening agents used for home bleaching without a prescription of a dentist, the concentration of hydrogen peroxide is regulated to 3% or less, in the case of general whitening agents which can be used at home under the supervision of a dentist, the concentration of hydrogen peroxide is regulated to 7 to 8%, and in the case of tooth whitening agent for experts who treat with dentistry, the concentration of hydrogen peroxide is regulated to 15% or less.

As described above, the home teeth whitening agents which can be used at home has a very low hydrogen peroxide concentration, and thus in an attempt to obtain a satisfactory tooth whitening effect, the effect can be seen only when they are repeatedly used several times over a long period of time, but the effect is very insignificant.

In such studies to complement the effect of the tooth whitening agent, an attempt has been made to promote the absorption of the whitening agent by using a peptide having a positive charge, but the effect thereof has not yet been verified.

SUMMARY OF THE INVENTION

In order to solve the problems of the prior arts as described above, it is one object of the present invention to provide a method for whitening teeth capable of promoting the whitening activity of a tooth whitening agent and increasing the degree of permeation of the whitening agent into teeth, thereby obtaining an excellent whitening effect.

In order to achieve the object above, the present invention provides a method for whitening teeth including the steps of coating a tooth whitening composition including a peroxide onto the teeth; and irradiating anions to the tooth whitening composition.

According to the tooth whitening method of the present invention, an excellent whitening effect can be obtained by promoting the whitening activity of a whitening agent such as peroxide and increasing the degree of permeation of the whitening agent into teeth. Accordingly, even when a low concentration of peroxide is used, an excellent whitening effect equivalent to or superior to that obtained by using hydrogen peroxide at a high concentration can be obtained.

Further, there is no risk of damaging the teeth, skin, nerves, mucous membranes, etc., and tooth whitening can be safely and easily performed at home, and thus it can be usefully applied not only to office bleaching but also to home bleaching.

In addition, the method for whitening teeth according to the present invention can be applied to conventionally known general-purpose whitening agents as well as specific whitening compositions and thus is expected to have a high utilization as a method for increasing whitening effects.

DETAILED DESCRIPTION OF THE EMBODIMENTS

In the present invention, it will be understood that, although the terms first, second, etc. may be used to describe various elements, and these terms are only used to distinguish one element from another element.

Further, the terminology used herein is for the purpose of describing particular embodiments only and is not intended to be limiting. As used herein, the singular forms "a," "an" and "the" are intended to include the plural forms unless the context clearly indicates otherwise. In the present disclosure, it will be further understood that the terms "comprise", "include", "have", etc. specify the presence of stated features, integers, steps, elements and/or combinations thereof but do not preclude the presence or addition of one or more other features, integers, steps, elements and/or combinations thereof.

In addition, in the present disclosure, it will be understood that when each layer or element is referred to as being formed "on" or "over" each of the layers or elements, each layer or element can be directly formed on each of the layers or elements, or another layer or element may be additionally formed between each layer, or on an object or substrate.

While a variety of modifications may be made to the present invention and there are various embodiments of the invention, examples of which will now be described in detail. However, this is not intended to limit the present invention to particular modes of practice, and it is to be appreciated that all modifications, equivalents and substitutions that do not depart from the sprit and technical scope of the invention are encompassed in the present invention.

Hereinafter, the method for whitening teeth according to the present invention will be described in more detail.

The method for whitening teeth according to the present invention includes the steps of coating a tooth whitening composition including a peroxide onto teeth; and irradiating anions to the tooth whitening composition.

First, a tooth whitening composition containing a peroxide is prepared and applied to the teeth.

The specific components of tooth whitening compositions slightly differ depending on the type of the composition, but they commonly contain peroxide as a whitening agent component for a whitening effect.

The peroxide is ionized in an aqueous solution to generate free radicals or superoxide and plays a role in decomposing pigment substances that cause tooth discoloration. As the peroxide, any substance conventionally used for tooth whitening in the technical field of the present invention can be used. For example, it may include hydrogen peroxide, perborate, percarbonate, superphosphate, persulfate, calcium peroxide, magnesium peroxide, carbamide peroxide and the like, and preferably, hydrogen peroxide may be used.

Figure 1:
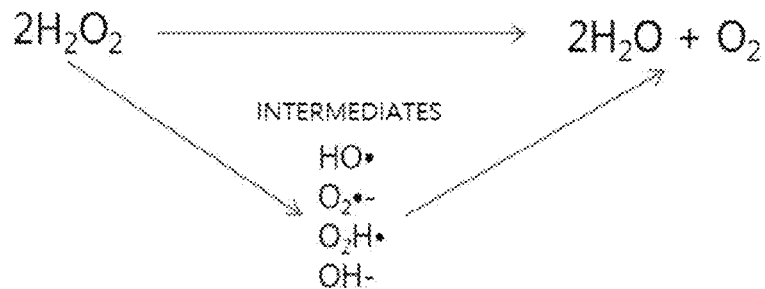
FIG. 1 is a schematic diagram showing a process by which hydrogen peroxide decomposes and functions.

FIG. 1 is a schematic diagram showing a process by which hydrogen peroxide in the tooth whitening composition decomposes and functions in whitening.

Referring to FIG. 1, the hydrogen peroxide in the tooth whitening composition is decomposed and converted into water and oxygen, and it is presented in several papers that various intermediates such as HO radicals. $O_2^-$ radicals and the like are involved in such decomposition process. Among them, the $O_2^-$ radical (superoxide, active oxygen) is a substance with a negative charge, and its half-life is prolonged in an electron-rich environment. As the half-life is prolonged, the reaction intermediates are formed more easily and as a result, the decomposition of hydrogen peroxide occurs more easily.

Based on such a finding, the present inventors have found that it helps the peroxides contained in the tooth whitening composition to permeate more into the teeth by the anion irradiation and that it enables the pigment decomposition to occur more effectively by creating an electron-rich environment for the permeated peroxides, thereby completing the present invention.

According to one embodiment of the present invention, the peroxide may be contained in an amount of about 1 to about 35% by weight based on the total tooth whitening composition.

Generally, as the concentration of peroxide contained in a tooth whitening composition increases, the permeation thereof into the teeth increases and the amount of peroxide that causes reaction increases, thereby exhibiting a greater tooth whitening effect. However, the concentration thereof is strictly limited due to safety concerns for human body. Depending on the use for home bleaching or office bleaching, for example, the concentration of peroxide in a tooth whitening composition acceptable in Korea is generally limited to 3 to 15% by weight, and up to 35% by weight may be allowed outside the country. In particular, in case of a home teeth whitening agent which can be used at home, and a general whitening agent used in the prescription of a dentist instead of a tooth whitening agent for experts who treat with dentistry, the content of peroxide contained therein is approximately 3 to 8% by weight, which is at a low concentration, and thus, a minimum effect can be seen only when they are repeatedly used several times for a long period of time, and even so, it may be difficult to obtain a satisfactory tooth whitening effect, which is problematic.

However, according to the method for whitening teeth of the present invention, even when a low concentration of peroxide is used, it is possible to obtain an excellent whitening effect equivalent to or rather superior to that obtained by using a whitening composition containing a high concentration of peroxide, such as a professional tooth whitening agent. Accordingly, because it shows an excellent whitening effect while securing the safety to the human body, it can be used for all tooth whitening performed without any help from a dentist or under the supervision of a dentist, without limitation.

According to one embodiment of the present invention, the tooth whitening composition may further include an electrolyte.

Electrolytes are substances that dissolve in water and dissociate into cations and anions, and any substance which is confirmed to be safe to the human body can be used without limitation. For example, it may include potassium phosphate ($K_3PO_4$, $K_2HPO_4$, $KH_2PO_4$), sodium chloride (NaCl), sulfuric acid ($H_2SO_4$), hydrochloric acid (HCl), sodium hydroxide (NaOH), potassium hydroxide (KOH) or sodium nitrate ($Na_2NO_3$), etc.

Among the electrolytes, an electrolyte, which has a high dissociation degree in water, can discharge more ions at the same concentration, and plays a role in increasing the pH, may exhibit a better effect.

For example, potassium triphosphate ($K_3PO_4$), when dissolved in water, is mostly dissociated to give three potassium ions, which are cations, per molecule, and phosphorus ions, which are anions, are present in one of three form $H_2PO_4^-$, $HPO_4^{2-}$, $PO_4^{3-}$. The forms and ratio of these anions are determined according to the pH range. Further, since potassium triphosphate has a pKa of 12.38, it increases the pH of a solution, and the higher the pH, the more unstable hydrogen peroxide is, and thus, it can promote the decomposition of hydrogen peroxide.

Accordingly, from this perspective, potassium triphosphate can be preferably used as the electrolyte.

The content of the electrolyte is not particularly limited, but it may be contained at a concentration of about 1 to about 100 mM, preferably, about 5 to about 50 mM.

According to the tooth whitening method of the present invention, when an irradiation of anions was applied to the whitening composition, which further includes the electrolyte in addition to the peroxide exhibiting a whitening activity, it was confirmed that the effect of the present invention as described above was further increased, that is, the permeation of peroxide into the teeth and the whitening activity were further increased.

When the tooth whitening composition further includes the electrolytes, the electrolytes may permeate into the surface and inside of the tooth by the difference in the concentration. As the electrolytes permeate into the inside of the teeth, it may act to promote the permeation of hydrogen peroxide, which is a substance that causes whitening, and may also act to push the pigment deposited on the inside of the tooth surface to the outside. When anions are irradiated thereto, it may further promote the movement of the electrolytes, thereby exhibiting an effect of pigment decomposition, or it may discharge the pigment deposited on the teeth, thereby bringing a greater whitening effect.

The tooth whitening composition may be in a state of an aqueous solution containing the peroxide by including water. The water content may be included in the remaining range excluding the peroxide and other additives.

In addition to the components described above, the tooth whitening composition of the present invention may further include an additive, such as a gelling agent, a pH adjusting agent, a stabilizer, a humectant, a chelating agent, a surfactant, a sweetening agent, a flavoring agent and the like, if necessary. As the additive, any material and content commonly used in the technical field to which the present invention pertains can be used, and are not particularly limited thereto.

The tooth whitening composition is evenly coated onto the surface of the teeth. The coating of the tooth whitening composition may be performed by a method of directly coating onto the teeth, or preliminarily coating or impregnating the tooth whitening composition to a substrate and attaching the substrate to the teeth, etc., but is not limited thereto.

Next, the coated tooth whitening composition is irradiated with anions.

Figure 2:
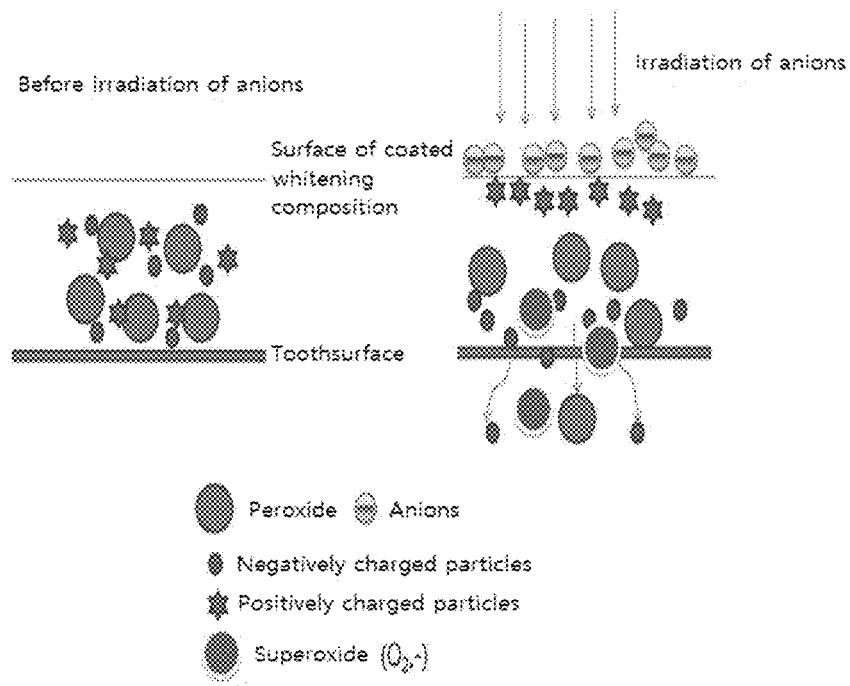
FIG. 2 is a schematic diagram showing a mechanism by which the irradiation of anions promotes the decomposition of hydrogen peroxide.

FIG. 2 is a schematic diagram showing a mechanism by which the irradiation of anions promotes the decomposition of hydrogen peroxide.

As described above, it can be said that the supply of electrons is important for effective permeation and decomposition of peroxides, which act as a tooth whitening agent.

According to the tooth whitening method of the present invention, the irradiation of anions increases both the degree of permeation of peroxide into the teeth and the activity of pigment decomposition, thereby obtaining a superior whitening effect.

Referring to FIG. 2, before coating the whitening composition onto the teeth and irradiating anions, peroxides, negatively charged intermediate particles and positively charged intermediate particles resulting from the decomposition of peroxides, $O_2^-$ radicals and the like are randomly present without a concentration gradient. Among them, statistically, the decomposition reaction occurs only by the intermediates attached to the surface of the teeth, and thus only a very small percentage of the peroxides in the whitening composition coated onto the teeth actually participates in the pigment decomposition reaction.

Meanwhile, as the anions are irradiated, the anions adhere to the surface formed by the whitening composition coated onto the teeth, and these anions pull the positively charged particles in the whitening composition and push away the negatively charged particles in the opposite direction. Accordingly, the surface of the tooth is built up with negatively charged particles, and the decomposition of peroxide is promoted in such an environment.

The type of an irradiator for irradiating the anions is not particularly limited as long as it can be applied to the human body. For example, a metal discharge method which includes electrodes for discharging and generates anions by a corona discharge in the cathode, a method of using carbon fibers, dielectric barrier discharge plasma and the like may be used.

Further, the irradiation time of the anions can be determined depending on the type and strength of the anion irradiator, the coloring of the teeth to be bleached, and the degree of a desired color, and can be generally irradiated for about 1 to 30 minutes, preferably, about 5 to 15 minutes. In order to achieve a more effective whitening effect, it is also possible to repeatedly coat the tooth whitening composition of the present invention one or more times within the irradiation time. After the irradiation of anions, the coated composition is rinsed by washing or the like.

According to the tooth whitening method of the present invention, an excellent whitening effect can be obtained by promoting the whitening activity of the whitening agent and increasing the degree of permeation of the whitening agent into the teeth, and accordingly, an excellent whitening effect equivalent to or superior to that obtained by using hydrogen peroxide at a high concentration can be obtained despite the use of low-concentration peroxide.

In addition, there is no risk of damaging the teeth, skin, nerves, mucous membranes, etc., and tooth whitening can be safely and easily performed at home, and thus it can be applied not only to office bleaching but also to home bleaching.

Hereinafter, the present invention will be described in more detail by way of specific Examples. However, these Examples are given for illustrative purposes only, and the scope of the invention is not intended to be limited by these Examples.

EXAMPLES

Anion Irradiation and Measurement Method of Whitening Effect

Figure 3:
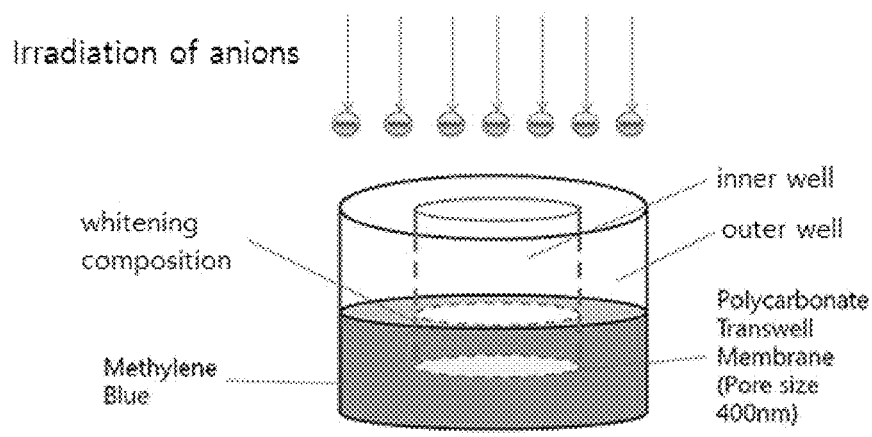
FIG. 3 is a schematic diagram showing an experimental apparatus which confirms the effect in accordance with the anion irradiation using a transwell membrane.

FIG. 3 is a schematic diagram showing an experimental apparatus which confirms the effect in accordance with the anion irradiation using a transwell membrane.

Referring to FIG. 3, the transwell membrane is divided into an outer well and an inner well. Further, it is designed such that, through a membrane, in which pores having a predetermined size are formed, at the bottom of the inner well, materials smaller than the size of the pore can move between the outer well and the inner well. In the present invention, a transwell membrane having a pore size of 400 nm was used, and the membrane was regarded as a tooth surface. For reference, the particle diameter of hydrogen peroxide and hydrogen peroxide decomposition intermediate materials are about 0.4 nm or less, the particle diameter of methylene blue used as a pigment is about 2 nm, and the size of the pore on the tooth surface is about 2000 to about 8000 nm.

Accordingly, through the membrane, hydrogen peroxide, hydrogen peroxide decomposition intermediate materials and methylene blue can move between the inner well and outer well, and when the membrane was regarded as a tooth surface, the whitening effect was confirmed by the decomposition (pigment decomposition) of the methylene blue on the tooth surface or on the inside via the anion irradiation, or by the movement thereof to the inner well (discharging the pigment to the outside).

As shown in FIG. 3, various tooth whitening compositions were put into the inner well of the transwell membrane and an aqueous solution containing methylene blue, which is a pigment, was put into the outer well, and then the transwell membrane was irradiated with anions for a predetermined time at room temperature. After the irradiation (or allowing to stand at room temperature in some cases of Comparative Examples), the degree of decomposition was measured by the concentration of methylene blue remained in the outer well, thereby examining the effect of the tooth whitening method according to the present invention.

Meanwhile, even when distilled water (DW) was injected into the inner well of the transwell membrane, and an aqueous solution of methylene blue of the same concentration and volume was put into the outer well and allowed to stand for 15 minutes without the anion irradiation, about 20% was lost. This was because the methylene blue was adsorbed onto the surface of the well. Thus, the degree of decomposition of methylene blue was calculated by excluding 20% as an adsorbed fraction in all Examples and Comparative Examples.

Example 1

An aqueous solution containing 15% by weight of hydrogen peroxide was prepared as a tooth whitening composition. As shown in FIG. 3, 100 µM of the composition was injected into the inner well of the transwell membrane, and 450 µM of an aqueous solution containing methylene blue at a concentration of 20 ppm was injected into the outer well.

The anions were irradiated to the thus-prepared transwell membrane at room temperature for 15 minutes using an anion irradiator (trade name: Bluen BN-108) positioned 15 cm away from the membrane.

Example 2

An anion irradiation was carried out in the same manner as in Example 1, except that an aqueous solution containing 15% by weight of hydrogen peroxide and 12.5 mM of potassium triphosphate ($K_3PO_4$) was prepared as a tooth whitening composition.

Example 3

An anion irradiation was carried out in the same manner as in Example 1, except that an aqueous solution containing 15% by weight of hydrogen peroxide and 25 mM of potassium triphosphate ($K_3PO_4$) was prepared as a tooth whitening composition.

Example 4

An anion irradiation was carried out in the same manner as in Example 1, except that an aqueous solution containing 3% by weight of hydrogen peroxide and 25 mM of potassium triphosphate ($K_3PO_4$) was prepared as a tooth whitening composition.

Example 5

An anion irradiation was carried out in the same manner as in Example 1, except that an aqueous solution containing 7% by weight of hydrogen peroxide and 25 mM of potassium triphosphate ($K_3PO_4$) was prepared as a tooth whitening composition.

Comparative Example 1

The transwell membrane was prepared in the same manner as in Example 1, but it was allowed to stand at room temperature for 15 minutes without irradiating anions.

Comparative Example 2

The transwell membrane was prepared in the same manner as in Example 3, but it was allowed to stand at room temperature for 15 minutes without irradiating anions.

Comparative Example 3

The transwell membrane was prepared in the same manner as in Example 4, but it was allowed to stand at room temperature for 15 minutes without irradiating anions.

Comparative Example 4

The transwell membrane was prepared in the same manner as in Example 5, but it was allowed to stand at room temperature for 15 minutes without irradiating anions.

Comparative Example 5

An anion irradiation was carried out in the same manner as in Example 1, except that an aqueous solution containing 15% by weight of hydrogen peroxide and 25 mM of propylene glycol was prepared as a tooth whitening composition.

Figure 4:
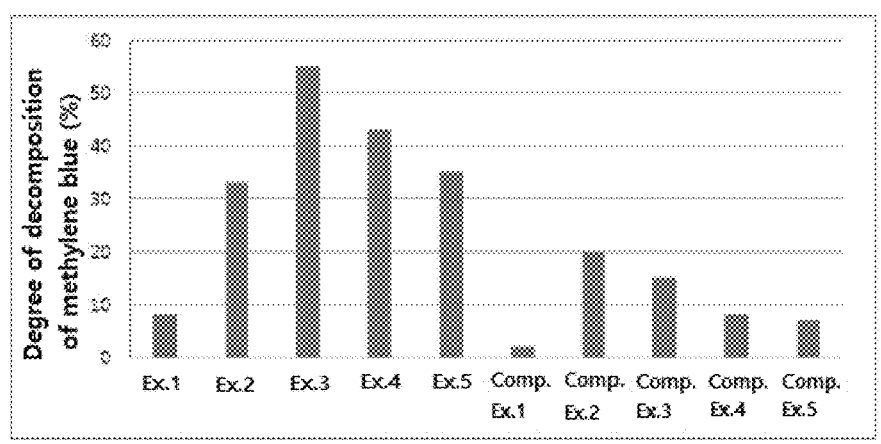
FIG. 4 is a graph showing the degree of decomposition of methylene blue of Examples and Comparative Examples of the present invention.

Experimental conditions for the Examples and Comparative Examples are summarized in Table 1 below. Further, a graph showing the degree of decomposition of methylene blue for each of the Examples and Comparative Examples is shown in FIG. 4.

TABLE 1

|  | Concentration of hydrogen peroxide | Type and concentration of electrolytes | Presence or absence of anion irradiation | Degree of decomposition of methylene blue |
| --- | --- | --- | --- | --- |
| Example 1 | 15% by weight | 0 mM | ○ | 8% |
| Example 2 | 15% by weight | potassium triphosphate, 12.5 mM | ○ | 33% |
| Example 3 | 15% by weight | potassium triphosphate, 25 mM | ○ | 55% |
| Example 4 | 7% by weight | potassium triphosphate, 25 mM | ○ | 43% |
| Example 5 | 3% by weight | potassium triphosphate, 25 mM | ○ | 35% |
| Comparative Example 1 | 15% by weight | 0 mM | X | 2% |
| Comparative Example 2 | 15% by weight | potassium triphosphate, 25 mM | X | 20% |

TABLE 1-continued

| | Concentration of hydrogen peroxide | Type and concentration of electrolytes | Presence or absence of anion irradiation | Degree of decomposition of methylene blue |
|---|---|---|---|---|
| Comparative Example 3 | 7% by weight | potassium triphosphate, 25 mM | X | 15% |
| Comparative Example 4 | 3% by weight | potassium triphosphate, 25 mM | X | 8% |
| Comparative Example 5 | 15% by weight | propylene glycol, 25 mM | ○ | 7% |

Experimental Examples

1) Evaluation on Degree of Permeation According to Anion Irradiation

In order to evaluate the degree of permeation of hydrogen peroxide into the teeth by the irradiation of anions, a composition containing 15% by weight of hydrogen peroxide and 25 nM of potassium triphosphate was prepared. As shown in FIG. 3, 200 µM of the composition was injected into the inner well of the transwell membrane, and 700 µM of the aqueous solution was injected into the outer well.

Two identical transwell membranes were prepared by the above-described process, and one of them was irradiated with anions at room temperature for 10 minutes using an anion irradiator (trade name: Bluen: BN-108), and the other one was allowed to stand at room temperature for 10 minutes without irradiating anions.

Thereafter, the concentration of hydrogen peroxide escaped from each transwell membrane to the outside was titrated to calculate the ratio of hydrogen peroxide that passed through the membrane. As a result, the ratio of hydrogen peroxide escaped from the anion-irradiated transwell membrane to the outside was 72% by weight, and the ratio of hydrogen peroxide escaped from the non-irradiated transwell membrane to the outside was 51% by weight.

From the experimental results above, it can be found that the degree of permeation of hydrogen peroxide into the membrane was increased by about 1.4-fold by the irradiation of anions.

2) Evaluation on Whitening Effect by Anion Irradiation

By comparing Examples 1, 3, 4 and 5 and Comparative Example 1, 2, 3, and 4, respectively, with reference to Table 1 above and FIG. 4, it was found that when the anions were irradiated to the whitening composition having identical components, or when the anions were not irradiated thereto, the degree of decomposition of methylene blue was increased by a minimum of 2.8-fold to a maximum of 7-fold.

The results of Experiments 1 and 2 demonstrate that the permeation of hydrogen peroxide into the teeth and the activity of pigment decomposition were both increased by the irradiation of anions 3) Evaluation on Whitening Effect According to Concentration By comparing Examples 1 to 3, it can be found that the degree of decomposition of methylene blue increased under the same conditions as potassium triphosphate was included as an electrolyte, and such an increasing effect in the degree of decomposition was proportional to the concentration of potassium triphosphate up to at least 25 mM.

Further, by comparing Examples 3 to 5, the degree of decomposition of methylene blue increased as the concentration of hydrogen peroxide increased under the same conditions. In particular, in the case of Example 5, it showed a high degree of decomposition of 34% even though only 3% by weight of hydrogen peroxide was contained, and this value was much higher than that of Comparative Example 1 which contained 15% by weight of hydrogen peroxide without the irradiation of anions.

What is claimed is:

1. A method for whitening teeth comprising the steps of:
    coating a tooth whitening composition including a peroxide onto the teeth; and
    irradiating anions to the tooth whitening composition.

2. The method for whitening teeth according to claim 1, wherein the tooth whitening composition further includes an electrolyte.

3. The method for whitening teeth according to claim 2, wherein the electrolyte includes at least one selected from the group consisting of potassium phosphate ($K_3PO_4$, $K_2HPO_4$, $KH_2PO_4$), sodium chloride (NaCl), sulfuric acid ($H_2SO_4$), hydrochloric acid (HCl), sodium hydroxide (NaOH), potassium hydroxide (KOH) and sodium nitrate ($Na_2NO_3$).

4. The method for whitening teeth according to claim 2, wherein the electrolyte is contained at a concentration of 1 to 100 mM.

5. The method for whitening teeth according to claim 1, wherein the peroxide includes at least one selected from the group consisting of hydrogen peroxide, perborate, percarbonate, superphosphate, persulfate, calcium peroxide, magnesium peroxide and carbamide peroxide.

6. The method for whitening teeth according to claim 1, wherein the peroxide is contained in an amount of 1 to 35% by weight based on the total weight of the tooth whitening composition.

* * * * *